US00PP32965P2

(12) United States Plant Patent
Clark

(10) Patent No.: US PP32,965 P2
(45) Date of Patent: Apr. 13, 2021

(54) BLACKBERRY PLANT NAMED 'A-2454T'

(50) Latin Name: ***Rubus* subgenus *Rubus* Watson**
Varietal Denomination: A-2454T

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/873,341

(22) Filed: Mar. 24, 2020

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 6/7499
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark et al. |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz et al. |
| PP26,405 | P3 | 2/2016 | Clark et al. |
| PP26,413 | P3 | 2/2016 | Ortiz et al. |
| PP26,990 | P3 | 8/2016 | Clark |
| PP27,032 | P2 | 8/2016 | Clark |
| PP27,401 | P3 | 11/2016 | Clark et al. |
| PP28,598 | P3 | 11/2017 | Clark |

OTHER PUBLICATIONS

Salgado et al, Characterization of Crispy Selections of the Arkansas Blackberry Breeding Program, published Jul. 28, 2014, Downloaded from researchgate.net/publication/267353660_Characterization_of_Crispy_Selections_of_the_Arkansas_Blackberry_Breeding_Program/citation/download on Sep. 8, 2020.*
U.S. Appl. No. 16/602,884, filed Dec. 18, 2019.
U.S. Appl. No. 16/602,892, filed Dec. 19, 2019.

* cited by examiner

*Primary Examiner* — Anne Marie Grunberg
(74) *Attorney, Agent, or Firm* — Quarles & Brady LLP

(57) ABSTRACT

Description and specifications of a new and distinct cultivar of blackberry plant named 'A-2454T' which originated from seed produced by a hand-pollinated cross 'Ark. 2252T' (a non-patented, unreleased genotype) x 'Ark. 2255' (a non-patented, unreleased genotype). This new cultivar of blackberry plant can be distinguished by its medium size, very firm berries with very sweet, sub-acid flavor, excellent postharvest fruit-handling potential, early season ripening, and excellent plant health.

2 Drawing Sheets

Latin name: *Rubus* subgenus *Rubus* Watson.
Varietal denomination: 'A-2454T'.

BACKGROUND

The new floricane-fruiting cultivar of blackberry called 'A-2454T' is described herein. The new cultivar originated from a hand-pollinated cross of 'Ark. 2252T' (a non-patented, unreleased genotype) x 'Ark. 2255' (a non-patented, unreleased genotype) made in 2004. The seeds resulting from this controlled hybridization were germinated in a greenhouse in the spring of 2005 and planted in a field near Clarksville, Ark. (West-Central Arkanas). The seedlings fruited in the summer of 2008 and one seedling, designated 'Ark. 2454T,' was selected for its medium size, very firm berries with very sweet, subacid flavor, excellent postharvest fruit-handling potential, early season ripening, and good plant health.

SUMMARY OF THE INVENTION

This new and distinct cultivar of blackberry originated from a hand-pollinated cross of 'Ark. 2252T' (a non-patented, unreleased genotype) x 'Ark. 2255' (a non-patented, unreleased genotype) made in 2004 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2005 and planted in a field near Clarksville, Ark. The seedlings fruited in the summer of 2008 on floricanes and one seedling, designated 'Ark. 2454T,' was selected for medium size, very firm berries with very sweet, subacid flavor, excellent postharvest fruit-handling potential, early season ripening, and good plant health.

During 2008, the original plant selection was propagated asexually from root cuttings at the above-noted location, and a test row of 20 plants was established. Subsequently, larger test plantings have been established with asexually multiplied plants at two locations in Arkansas.

The new cultivar has been asexually multiplied annually since 2008 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants from which the images were taken were 3 years old.

DETAILED DESCRIPTION OF THE NEW CULTIVAR 'Ark-2454T'

Figure 1:
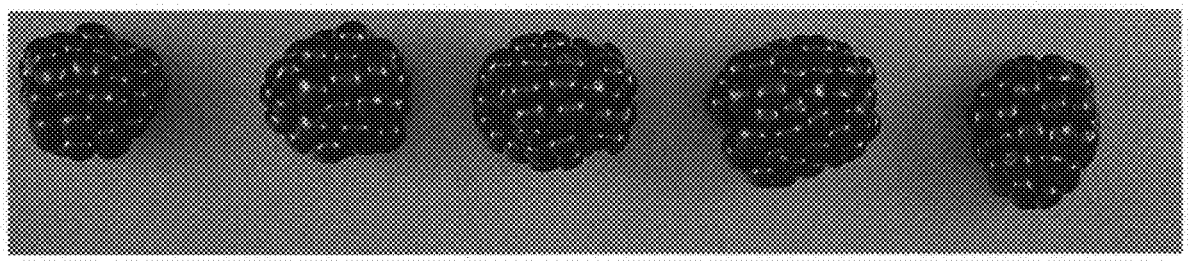
FIG. 1 is a photograph of ripe fruit of 'Ark-2454T'.
Figure 2:
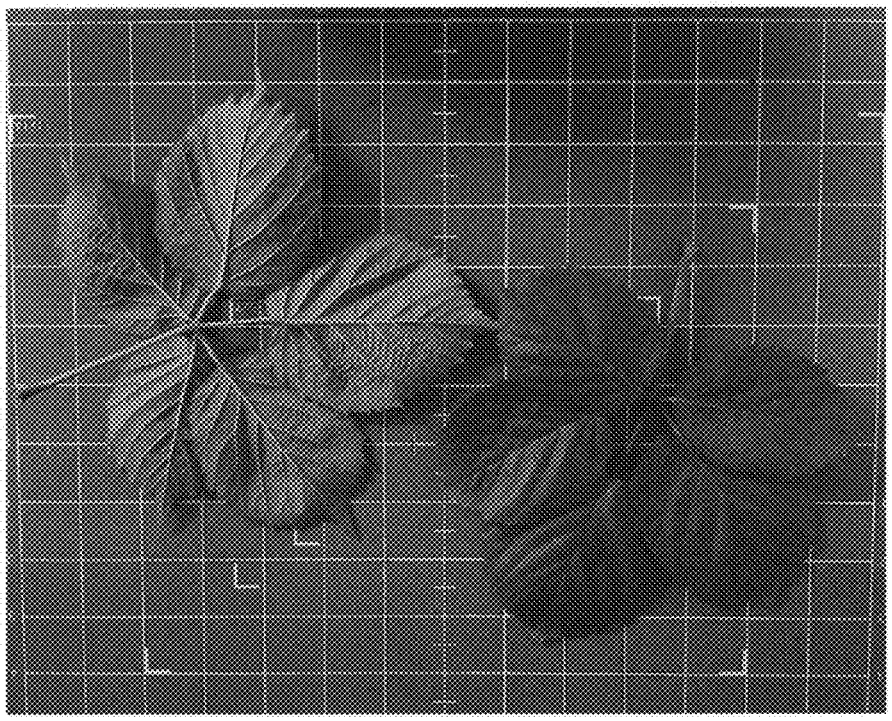
FIG. 2 is a photograph showing the abaxial and adaxial sides of a primocane leaf of 'Ark-2454T'.

Plants and fruit of this new cultivar differ phenotypically from its parents. The new cultivar is larger in fruit size and more firm than its female parent 'Ark. 2252T.' The new cultivar is earlier ripening, is more firm, and has much sweeter fruit than its male parent 'Ark. 2255'. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit have shown slight susceptibility to anthracnose [*Elsinoe veneta* (Burkh.) Jenkins], and plants have shown no evidence of susceptibility to orange rust [*Gymnoconia nitens* (Schwein.) F. Kern and H. W. Thurston.]. Plants have shown susceptibility to cane and leaf rust (*Kuehneola uredines* (Link) Arthur). No screening has been done for resistance to double blossom/rosette [*Cercosporella rubi* (Wint.) Plakidas]

The bloom period of the new cultivar begins on average 11 April for 10% bloom and 20 April for 50% bloom and was very near that of 'Osage' (U.S. Plant Pat. No. 26,120) and later than 'Natchez' (U.S. Plant Pat. No. 20,891).

Fruit of the new cultivar has an average first harvest date of 25 May and was five days earlier than 'Natchez' seven days earlier than 'Osage'. The average floricane fruiting period is 60 days.

Fruit yields of the new cultivar on floricanes are on average 4.2 kg (9.2 lb/plant), slightly less than that for 'Osage' and near half of that of 'Natchez', in West-Central Arkansas. Fruit yields were reduced by one-half when winter temperatures of 9° F. (−13° C.) were experienced in the winter prior to fruiting, indicating susceptibility to mid-winter bud and cane injury, compared to 'Osage' that had no crop reduction. Secondary buds have been observed on canes that had bud injury from mid-winter low temperatures.

The fruit is round in shape and glossy with a uniform black finish. The floricane fruit is medium (ave. 5.8 g), slightly larger than 'Osage', and 4 g smaller than 'Natchez'. Fruit size of the new cultivar is maintained well throughout the entire harvest season. The new cultivar exhibits excellent fruit fertility with full drupelet set. Fruit firmness is a noteworthy characteristic and is near crisp in texture, and was consistent whether in rainy or dry periods of fruit maturity. Storage potential of fresh fruit of the new cultivar exceeds that of 'Osage' and far exceeds that of 'Natchez'.

The dry seed weight for the new cultivar averaged 3.8 mg/seed, the same as 'Osage' and much smaller than 'Natchez' of 10 g.

The fresh fruit rates very well in flavor and is a noteworthy attribute of the cultivar and is comparable to or exceeding that of 'Osage', and 'Natchez'. Consistent flavor was noted at repeated observations of fruit of this cultivar over the years of evaluation including after rain events that can reduce flavor and overall fruit quality. The flavor is sweet and sub-acid. The soluble solids concentration averages 11.1% on shiny black fruit, which is higher than 'Osage', and 'Natchez'. Titratable acidity averages 0.60 g/L (expressed as citric acid) and is lower than that for 'Osage' (0.89 g/L) and much lower than 'Natchez' (1.14 g/L). Red drupelet reversion was very low and lower than 'Osage' and much lower than 'Natchez'. The overall postharvest storage potential of fresh fruit of the new cultivar is greater than that of 'Osage and 'Natchez'. Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with drip irrigation at or near Clarksville, Ark. The plants were fertilized near budbreak (late March on average) with complete or nitrogen fertilizer and had an additional nitrogen fertilizer application in early July. Primocanes were tipped at approximately 1.14 m (45 inches) and grown in a hedgerow training system including a trellis. Weeds were controlled with pre- and post-emergent herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size.*—Medium. Plants are grown in a hedgerow and primocanes tipped at approximately 1.14 m; plants in this system range in size from approx. 107-140 cm tall and 91-102 cm wide.

*Growth habit.*—Upright, moderate vigor, canes erect; suckers from the crown and roots.

*Growth rate.*—Floricane first budbreak 11 February.

Productivity:

*Floricane.*—4.2 kg (9.2 lb/plant) when no winter injury was experienced. Fruit yields were reduced by one-half when winter temperatures of 9° F. (−13° C.) were experienced in the winter prior to fruiting, indicating susceptibility to mid-winter bud and cane injury.

*Primocane.*—No primocane fruiting was observed.

*Cold hardiness.*—Hardy to 17.0° F. (−8° C.). Temperatures lower than this have resulted in crop reduction.

Canes: thornless, erect:

*Floricane* (*dormant or winter cane*).—Cane: diameter: Base 1.65 cm; midpoint 1.38 cm; terminal 1.17 cm. Cross-section of dormant canes: round to angular. Internode length: Base 8.83 cm; midpoint 8.56 cm; terminal 5.42 cm. Floricane color: Greyed red (178A); midpoint greyed red (187A); terminus greyed red (187A). Glandular hairs on young shoots: absent.

*Primocane* (*current-season cane; late summer*).—Cane: Diameter: base 1.52 cm; midpoint 1.41 cm; terminal 0.86 cm. Internode length: Base 12.56 cm; midpoint 11.23 cm; terminal 6.38 cm. Primocane color: Base Yellow Green Group (144A) midpoint Yellow Green Group (144A); terminus Greyed Orange Group (175A). Anthocyanin coloration present on floricanes and primocanes with color most prevalent on sun-exposed canes. Thorn density (per 30 cm of cane length): None, this plant is thornless. Disease resistance: Plants and fruit have shown slight susceptibility to anthracnose, and plants have shown no evidence of susceptibility to orange rust. Plants have shown susceptibility to cane and leaf rust. No screening has been done for resistance to double blossom/rosette. Lateral branching after tipping (measured at the end of growing season): Average number of lateral branches: 4; distribution concentrated on the distal portion (top third) of the canes. Number: averaged 6 new canes per year. Glandular hairs on young shoots: absent.

Foliage:

*Primocane.*—Leaves: Large; mature compound leaf width 22.39 cm; length 20.15 cm; overall shape: palmate. Average date of leaf bud burst: 11 February. Glossiness: Abaxial: dull, not glossy; adaxial: dull, not glossy. Leaflet: Width 9.94 cm; length 10.39 cm; shape ovate with acute apex and rounded base; margin serrated, serration teeth length 0.36 cm and width 0.27 cm; number of leaflets per compound leaf 5; venation pinnate; young leaf abaxial vein color Yellow Green Group (145D); young leaf adaxial vein color Yellow Green Group (145B); mature leaf abaxial leaf vein color Yellow Green Group (145B); mature leaf adaxial vein color Yellow Green Group (145C); no lobing on leaflets; terminal leaflet cross-section is V-shaped; undulation is absent on the terminal leaflet margin; terminal leaflet blistering is absent to mildly present with younger leaves having more blistering and older leaves having a smooth leaf texture. Color: Base abaxial Green Group (137A); adaxial Green Group (137C); midpoint abaxial Green Group (137A); adaxial Green Group (137C); terminal abaxial Green Group (137A); adaxial Green Group (137C). Petioles: Length: 6.13 cm; color: adaxial Red Purple Group (60B) and abaxial Yellow Green Group (144B); diameter 0.34 cm; texture is mostly smooth, exhibiting light pubescence. Petiolules: Length: 3.81 cm; diameter 0.24 cm; color: abaxial Red Purple Group (60B) and adaxial Yellow Green Group (144B); texture is light pubescence. Stipules: 2 per leaf; Length: 1.16 cm; width: 0.10 cm; texture pubescence is present on the adaxial surface of all primocane stipules, but not on the abaxial surface; shape: overall shape is subulate; apex acuminate; base rounded; margins are smooth; Color: abaxial are Yellow Green Group (147B), adaxial color Green Group (143A).

*Floricane.*—Leaves: Large; mature compound leaf width 11.19 cm; length 11.70 cm. Glossiness: Abaxial: dull, pubescence lightly present; adaxial: dull, little to no pubescence. Leaflet: Width 5.63 cm; length 7.56 cm; shape ovate with acute apex and oblique base; margin serrated, with serration teeth length 0.31 cm and width at base 0.31 cm; number of leaflets per compound leaf 3; venation pinnate; young leaf abaxial vein color Yellow Green Group (145C); young leaf adaxial vein color Yellow Green Group (145C); mature leaf abaxial leaf vein color Yellow Green Group (149C); mature leaf adaxial vein color Yellow Green Group (149A); no lobing on leaflets; terminal leaflet cross-section is V-shaped; undulation is absent on the terminal leaflet margin; terminal leaflet blistering is absent to mildly present with younger leaves having more blistering and older leaves having a smooth leaf texture. Color: base abaxial Green Group (137A); adaxial Yellow Green Group (146B); midpoint abaxial Green Group (137A); adaxial Yellow Green Group (146B); terminal abaxial Green Group (137A); adaxial Yellow Green Group (146B). Petioles: Length 3.70 cm; color: abaxial side is Red Purple Group (59D); adaxial surface is Green Group (135A); diameter 0.19 cm; texture smooth, light pubescence present. Petiolules: Length 1.16 cm; diameter 0.15 cm; color: abaxial surface is Green Group (138C), adaxial surface is Green Group (137D); texture smooth with light pubescence. Stipules: 2 per leaf; length 0.64 cm; width: 0.11 cm; texture is smooth with no pubescence on the abaxial surface and light pubescence on the adaxial surface. Shape: overall shape subulate; apex acuminate; base rounded; margin is serrated; color: abaxial surface Yellow Green Group (147B), adaxial surface Green Group (138A).

Flowers:

*Floricane.*—Date of bloom: First bloom: 11 April; 50% bloom 20 April. Reproductive organs: Stamens — erect, numerous. Pistils — numerous. Pollen — normal, fertile, and abundant. Flower: Diameter: 3.24 cm; depth: 1.66 cm; shape: overall: rotate; symmetry: actinomorphic. Petals: Number per flower: 5; length 1.49 cm; width 1.07 cm; shape: apex: rounded; margin: entire (smooth); base: rounded; color: abaxial surface Red Group (36A) adaxial surface Red Group (36D); texture: abaxial: smooth, no pubescence; adaxial: smooth, no pubescence. Peduncle: color: Red Purple Group (60B). Cyme: Type: elongated simple cyme.

Fruit:

*Maturity.*—Average first ripe date 25 May; Average fruiting period 60 days.

*Size.*—Medium, ave. 5.8 g.

*Diameter of fruit at primary position on inflorescence.*—Equator 2.06 cm; base pole 1.71 cm; terminal pole 1.73 cm.

*Diameter of fruit at secondary positions on inflorescence.*—Equator 1.98 cm; base pole 1.63 cm; terminal pole 1.90 cm.

*Primary fruit.*—Length: 2.18 cm; shape: rounded; color: Black Group (202A).

*Drupelet size.*—0.65 cm.

*Drupelet number per fruit.*—37.

*Seed.*—Average length 0.31 cm; width 0.25 cm; dry weight 3.8 mg; wet weight 4.0 mg; color wet Greyed Orange Group (165C); color dry Greyed Yellow Group (162C).

*Soluble solids.*—11.1%.

*pH.*—3.67.

*Titratable acidity.*—0.60 g/L expressed as citric acid.

*Processed quality.*—Not evaluated for processing.

*Uses.*—Commercial cultivar with excellent potential for shipping, as well as an option for local-market production as well as home gardens.

The cultivar: The most distinctive features of the cultivar are medium size, very firm berries with very sweet, subacid flavor, excellent postharvest fruit-handling potential, early season ripening, and excellent plant health.

I claim:

1. A new and distinct cultivar of blackberry plant named 'A-2454T' substantially as illustrated and described herein.

* * * * *